United States Patent
McCurry et al.

(10) Patent No.: US 10,879,504 B2
(45) Date of Patent: Dec. 29, 2020

(54) ELECTRODE FEEDTHRU HAVING PIN ATTACHED TO WIRE THEREIN AND METHOD OF MANUFACTURING

(71) Applicant: Pacesetter, Inc., Sylmar, CA (US)

(72) Inventors: Troy L. McCurry, West Union, SC (US); Ralph Jason Hemphill, Sunset, SC (US); Peter Fernstrom, Easley, SC (US); Tearl Stocker, Easley, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 16/655,522

(22) Filed: Oct. 17, 2019

(65) Prior Publication Data

US 2020/0052251 A1 Feb. 13, 2020

Related U.S. Application Data

(62) Division of application No. 15/421,582, filed on Feb. 1, 2017, now Pat. No. 10,510,998.

(51) Int. Cl.

| | | |
|---|---|---|
| *H01M 2/06* | (2006.01) | |
| *H01R 13/52* | (2006.01) | |
| *H01G 9/10* | (2006.01) | |
| *A61N 1/375* | (2006.01) | |
| *H01G 9/008* | (2006.01) | |
| *H01G 9/06* | (2006.01) | |
| *H01R 13/74* | (2006.01) | |
| *H01R 4/18* | (2006.01) | |

(52) U.S. Cl.
CPC ............ *H01M 2/06* (2013.01); *A61N 1/3754* (2013.01); *H01G 9/008* (2013.01); *H01G 9/06* (2013.01); *H01G 9/10* (2013.01); *H01R 13/5205* (2013.01); H01M 2220/30 (2013.01); H01R 4/184 (2013.01); H01R 13/74 (2013.01)

(58) Field of Classification Search
CPC ........ A61N 1/3956; H01G 9/048; H01G 9/10; H01M 2220/30; H01M 2/06; H01R 13/5205; H01R 4/187
See application file for complete search history.

(56) References Cited

U.S. PATENT DOCUMENTS

| | | |
|---|---|---|
| 7,696,002 B1 | 4/2010 | Ribble et al. |
| 8,675,338 B2 | 3/2014 | Teske |
| 2006/0279906 A1 | 12/2006 | Stemen et al. |
| 2012/0205150 A1 | 8/2012 | Pretzlaff et al. |

*Primary Examiner* — Adam A Arciero
(74) *Attorney, Agent, or Firm* — Lerner, David, Littenberg, Krumholz & Mentlik, LLP

(57) ABSTRACT

Disclosed herein is an electrode feedthru assembly for an electronic device and method of manufacturing. The feedthru assembly includes a ferrule, an electrode assembly, and an elastomer. The ferrule includes a bore through which the electrode assembly is positioned. The electrode assembly includes an electrode wire attached to a crimp pin. The crimp pin includes a crimp terminal portion and a pin terminal portion, the crimp terminal portion crimped to the a portion of the electrode wire to form a connected portion of the electrode assembly. The elastomer is disposed in the bore of the ferrule between the ferrule and the electrode assembly. The elastomer is configured to electrically isolate the ferrule from the electrode assembly and to encapsulate at least the connected portion of the electrode assembly.

12 Claims, 10 Drawing Sheets

ELECTRODE FEEDTHRU HAVING PIN ATTACHED TO WIRE THEREIN AND METHOD OF MANUFACTURING

PRIORITY CLAIM

This application is a Continuation application of U.S. patent application Ser. No. 15/421,582, filed 1 Feb. 2017, entitled "System for Repeated Delivery of Implantable Devices", and is incorporated herein by reference in its entirety to provide continuity of disclosure.

BACKGROUND OF THE DISCLOSURE

Field

The present disclosure relates to a feedthru assembly for an electronic device and, more particularly, to an electrode feedthru assembly for use in an electrolytic device such as a capacitor or a battery. The present disclosure also relates to methods of manufacturing such an electrode feedthru assembly and a housing that incorporates the electrode feedthru assembly.

Background

Compact, high voltage capacitors and batteries are utilized as energy storage reservoirs in many applications, including implantable medical devices. They are required to have a high energy density, since it is desirable to minimize the overall size of the implanted device. This is particularly true of capacitors and batteries used in an Implantable Cardioverter Defibrillator (ICD), also referred to as an implantable defibrillator, since these devices can occupy a significant amount of space in an ICD.

Electrolytic capacitors are used in ICDs because they have preferable properties in terms of size, reliability, and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is typically used for the anode foils, other metals such as tantalum, magnesium, titanium, niobium, zirconium and zinc may be used.

A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent.

Electrolytic capacitors are typically formed into flat or cylindrical shapes. For a flat construction, the individual cathode and anode foils or plates are stacked in an interleaved manner with separators interposed there between, and the stack is encased in an aluminum case. For a cylindrical construction, the stacked plates are rolled up into the form of a substantially cylindrical body, or wound roll, that is held together with adhesive tape and is encased, with the aid of suitable insulation, in an aluminum tube or canister. In both flat and cylindrical constructions, connections to the anode and the cathode are made via tabs that extend outward from the stack or roll. An aluminum wire may then be connected (e.g., via welding) to each tab.

A feedthru assembly, also referred to as a "feed thru," "feedthrough," or "feed through" (sometimes hyphenated) assembly, is commonly used to pass an electrode through the case in which capacitor plates are held. Typically, a feedthru assembly is manufactured via a manual assembly method or an injection molding method. In a manual method, an aluminum wire is pulled through the center of a rubber gasket assembly. Next, the aluminum wire and rubber gasket assembly are pulled through a ferrule that has been welded or manufactured into a capacitor case. The aluminum wire on the inside of the case is then welded to a tab on either the anode plates or cathode plates.

The feedthru assembly provides an electrode connection between the anode plates, or the cathode plates, inside the capacitor case to an electrical device on an outside of the capacitor case, while preventing the electrolyte from leaking from the case. The manual assembly method is robust and has a low leak rate, but a highly skilled operator is required to perform this operation, preventing automated manufacturing of the feedthru assembly. Further, the rubber feedthru material can have high variability in the material sealing properties and can be a source of contamination for the capacitor. Both issues can lead to a decrease in yield due to electrolyte leaking out of the case and capacitor failure due to contamination.

In an injection molding method, an elastomer is formed between an electrode, such as a wire or pin, and a ferrule to create an insert molded feedthru assembly. This method is more production friendly, as compared to the manual method. However, both methods produce a feedthru with low tensile strength that is easily damaged, because the wire or pin conductor that goes through the feedthru is easily broken. This problem is particularly acute in an aluminum electrolytic capacitor where the wire or pin must be formed of a high purity aluminum to be compatible with the chemistry of the capacitor. High purity aluminum has a low tensile strength and therefore may be easily broken during manufacturing or later handling or use.

What is needed is a feedthru that is more easily manufactured and less susceptible to damage.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 1A:
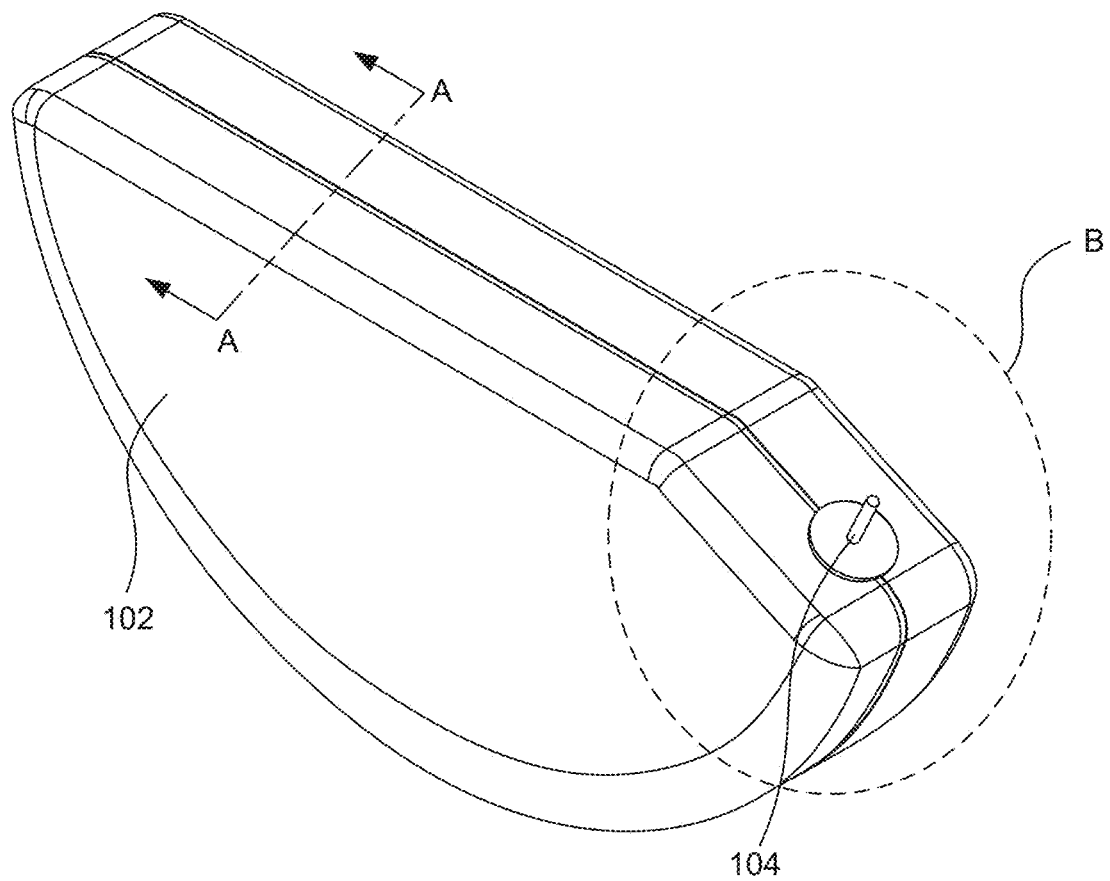
FIG. 1A is a perspective view of an electrolytic capacitor, according to an embodiment of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION

The following detailed description of feedthru assemblies and methods of manufacturing refers to the accompanying drawings that illustrate exemplary embodiments consistent with these apparatuses and methods. Other embodiments are possible, and modifications may be made to the embodiments within the spirit and scope of the apparatuses and methods presented herein. Therefore, the following detailed description is not meant to limit the apparatuses and methods described herein. Rather, the scope of these methods and systems is defined by the appended claims.

It would be apparent to one of skill in the art that the feedthru assemblies and methods of manufacturing, as described below, may be implemented in many different embodiments without departing from the scope of the description below. Thus, the operation and behavior of the apparatuses and methods will be described with the understanding that modifications and variations of the embodiments are possible, given the level of detail presented herein. For example, while the following embodiments describe a feedthru assembly connected to an anode of a capacitor, the feedthru assembly of the present disclosure may be connected to other elements such as a cathode and/or be in other electrical devices such as a battery. It will be apparent to a person skilled in the relevant art that the apparatuses and methods may also be employed to produce feedthru assemblies for use in a variety of devices and applications in addition to use in an implantable cardioverter defibrillator (ICD).

Figure 1B:
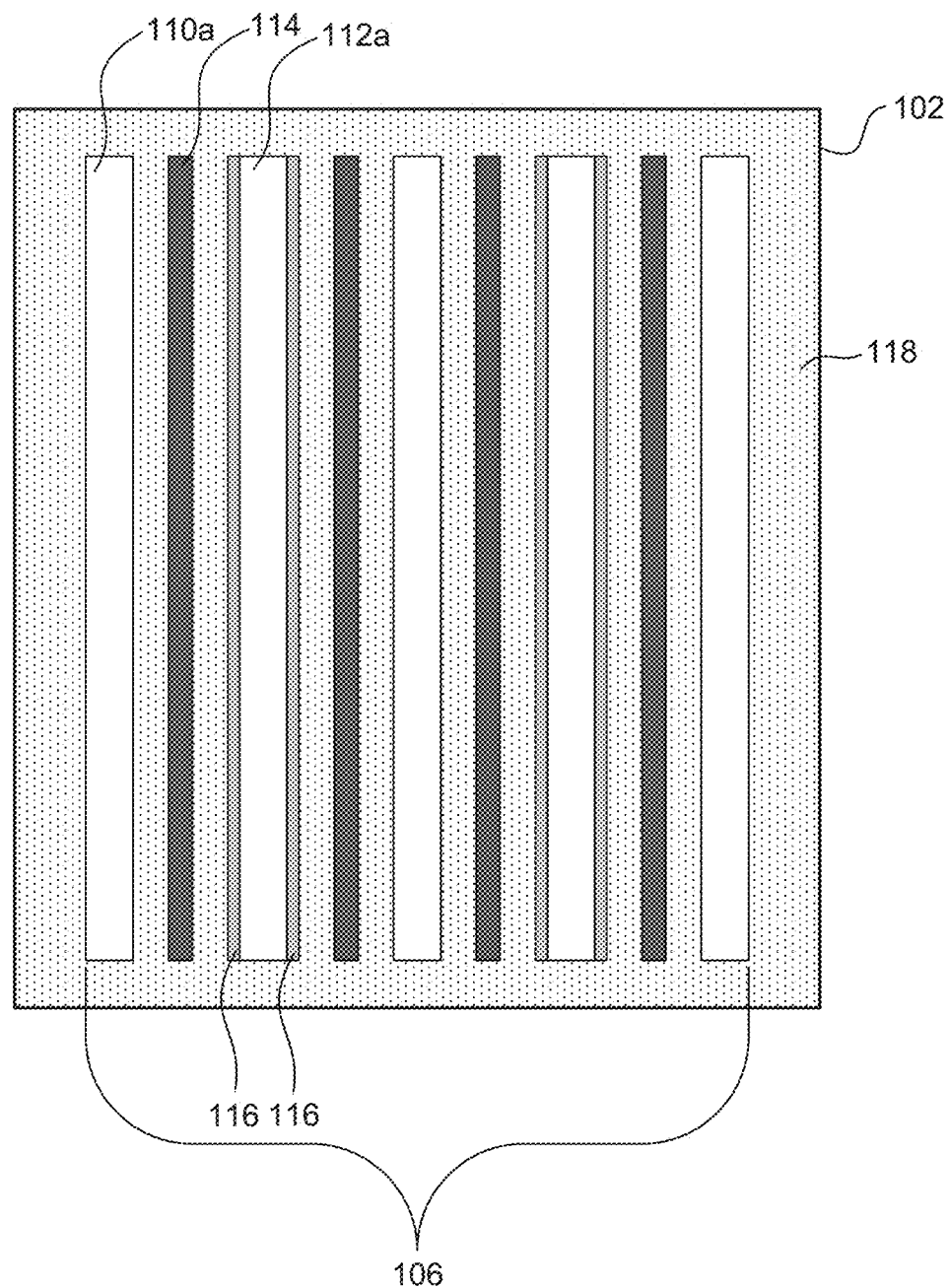
FIG. 1B is a schematic diagram illustrating a cross-section of the electrolytic capacitor of FIG. 1A, according to an embodiment of the present disclosure.
Figure 1C:
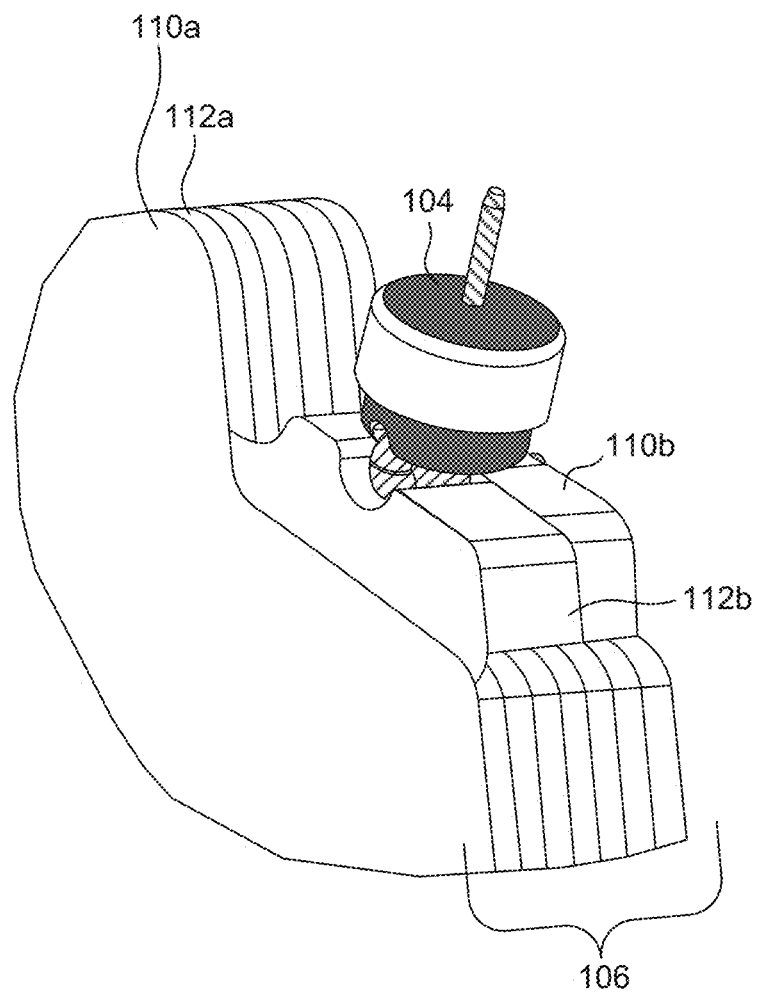
FIG. 1C is a partial, cut-away view of portion B of the electrolytic capacitor of FIG. 1A illustrating a feedthru assembly, according to an embodiment of the present disclosure.

FIGS. 1A-1C illustrate different views of an electrolytic capacitor 100, according to an embodiment of the present disclosure. As shown by FIG. 1A, electrolytic capacitor 100 includes a housing 102 and a feedthru assembly 104. Housing 102 encloses and provides protection for elements within housing 102 and, in some embodiments, acts as an electrical connection for an anode or a cathode contained within housing 102. Housing 102 may be formed of a material such as aluminum or stainless steel. However, it would be apparent to one skilled in the art that a variety of other metals or materials may be used to form housing 102. While FIGS. 1A-1C depict housing 102 and electrolytic capacitor 100 formed in a D-shape, other shapes would be understood by one skilled in the art.

As shown by FIG. 1B, housing 102 contains a capacitor stack 106, also referred to as an anode/cathode stack, that includes a plurality of cathode plates 110a that alternate with a plurality of anode plates 112a, and are separated by a plurality of separators 114. Each of the plurality of cathode plates 110a includes a tab 110b, as shown by FIG. 1C. Tabs 110b for the plurality of cathode plates 110a are connected together, for example, through a welding process, to form a single, common cathode (the collection of electrically connected cathode plates 110a are referred to herein as cathode 110). Likewise, each of the plurality of anode plates 112a includes a tab 112b, and tabs 112b for the plurality of anode plates 112a are connected together, for example, through a welding process, to form a single, common anode (the collection of electrically connected anode plates 112a are referred to herein as anode 112). Example materials used for the cathode 110 include aluminum, titanium, stainless steel, while example materials for the anode 112 include aluminum and tantalum.

A dielectric material 116 may be disposed on or around an outer surface of anode plate 112a. Dielectric material 116 may be an oxide that is thermally grown on, or deposited onto, the surface of each anode plate 112a. A high-k (i.e., a high-dielectric constant) dielectric material may be used for dielectric material 116.

The plurality of separators 114 maintain a given separation between each cathode plate 110a and an adjacent anode plate 112a within housing 102. Additionally, the plurality of separators 114 prevent arcing between cathode plate 110a and anode plate 112a in spaces where dielectric material 116 may be very thin or nonexistent, and/or where a void within electrolyte 118 exists between cathode plate 110a and anode plate 112a. The plurality of separators 114 may be formed of kraft paper or fabric gauze impregnated with a solvent-based liquid electrolyte.

A conductive electrolyte 118 fills the space between each of the elements within housing 102. Electrolyte 118 may be a polymer or liquid electrolyte as would be understood by one skilled in the art. Example electrolytes include ethylene glycol/boric acid based electrolytes and anhydrous electrolytes based on organic solvents such as dimethylformamide (DMF), dimethylacetamide (DMA), or gamma-butyrolactone (GBL).

It should be understood that the various elements and dimensions of capacitor 100 are not drawn to scale. Although cathode plates 110a, anode plates 112a, and separators 114, are illustrated as being spaced apart from one another for the convenience of illustration and labeling, it would be understood by one skilled in the art that such elements may also be stacked together in close physical contact with one another.

As shown by FIG. 1A, Housing 102 further comprises an aperture through which feedthru assembly 104 is disposed. The aperture may be formed by stamping, laser cutting, drilling, beveling, or any other known method. Further, the aperture of housing 102 may be formed into shapes other than a circle, as would be apparent to one skilled in the art.

Feedthru assembly 104 is configured to provide an electrical connection between anode 112 and an external component (not shown) of an ICD, such as the electrical circuitry within an ICD or other implantable medical device, while electrically isolating anode 112 and the electrical connection thereto from housing 102 (which may be electrical connected to cathode 110). Feedthru assembly 104 is further configured to prevent leakage of electrolyte 118 from housing 102.

Figure 2:
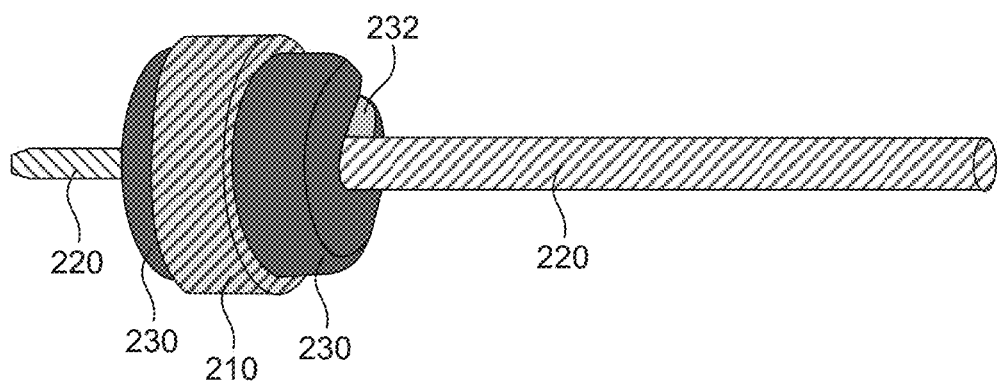
FIG. 2 is a perspective view of a feedthru assembly, according to an embodiment of the present disclosure.
Figure 3:
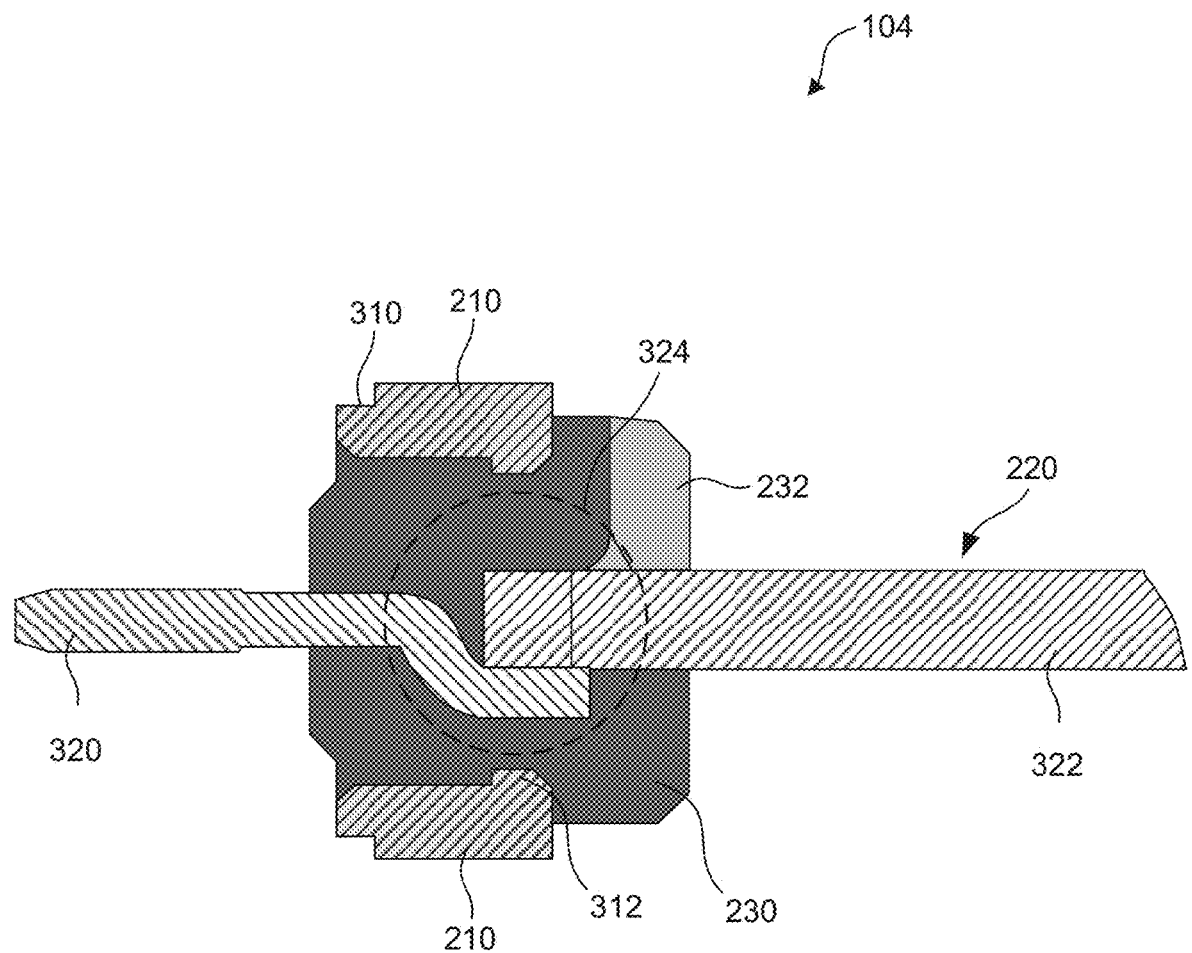
FIG. 3 is a cross-sectional view of the feedthru assembly of FIG. 2, according to an embodiment of the present disclosure.
Figure 4:
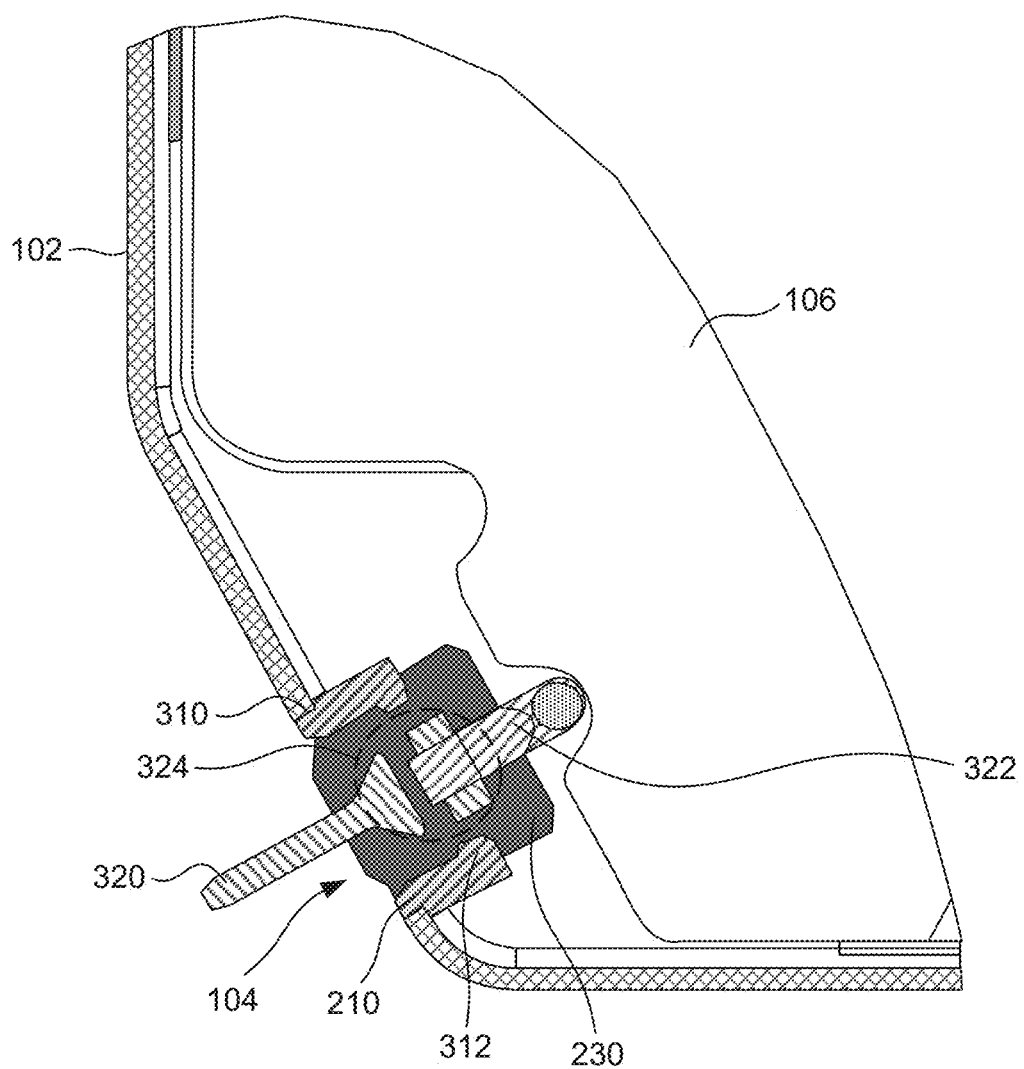
FIG. 4 is a partial cross-sectional view of the electrolytic capacitor of FIG. 1C, according to an embodiment of the present disclosure.

FIGS. 2-4 illustrate different views of feedthru assembly 104 both assembled with and isolated from housing 102, and are used below in describing feedthru assembly 104.

Figure 5A:
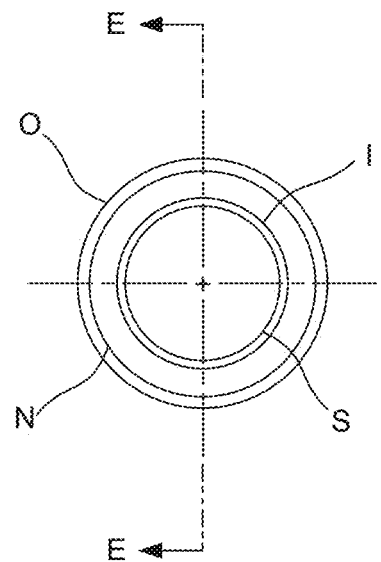
FIG. 5A is an end view of a ferrule, according to an embodiment of the present disclosure.
Figure 5B:
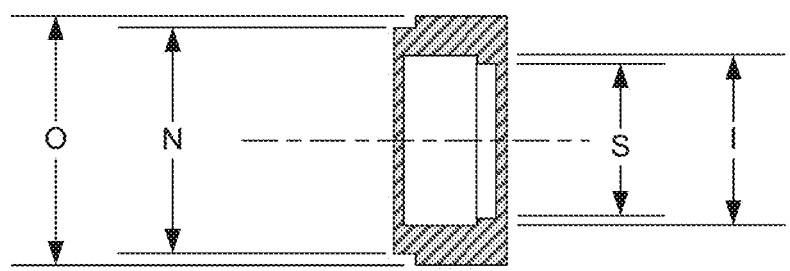
FIG. 5B is a cross-sectional view of the ferrule of FIG. 5A taken across section line E-E of FIG. 5A, according to an embodiment of the present disclosure.

As shown, feedthru assembly 104 includes a ferrule 210, an electrode assembly 220, and an elastomer structure 230. Ferrule 210 is a tubular structure configured to be disposed within the aperture of housing 102, as shown by FIG. 4. FIGS. 5A-5B show additional views of ferrule 210. FIG. 5A illustrates an end view of ferrule 210, and FIG. 5B illustrates a cross-sectional view of the ferrule 210 taken along section line E-E of FIG. 5A. An outside surface of ferrule 210 is configured to attach to housing 102 within the aperture by, for example, a welding process to prevent leakage of electrolyte 118 between ferrule 210 and housing 102. Ferrule 210 is formed of a material configured to bond and seal to housing 102 and as such may be formed of the same material as housing 102 such as aluminum or stainless steel. However, it would be apparent to one skilled in the art that a variety of other metals or materials may be used.

In an embodiment, ferrule 210 has a stepped-shape formed from a reduced diameter portion or notch 310, as shown by FIGS. 3 and 4. Notch 310 facilitates placement of feedthru assembly 104 to a desired depth within the aperture of housing 102. As shown by FIGS. 5A-5B, ferrule 210 may include a shoulder diameter size O which is greater than a notch diameter size N of notch 310, as shown by FIG. 5B. Because of the reduced diameter size N of notch 310, the feedthru assembly 104 sets within the aperture of housing 102 such that only a portion of ferrule 210 is exposed to an exterior of housing 102.

Ferrule 210 also includes an inner shoulder 312, as shown by FIGS. 3 and 4. Shoulder 312 aids in securing elastomer 230 in ferrule 210. As such, shoulder 312 includes a portion of ferrule 210 that protrudes into elastomer 230. Shoulder 312 may be formed from a reduced diameter portion of ferrule 210 that extends around a circumference of an inner surface of ferrule 210. As shown by FIGS. 5A-5B, shoulder 312 has a diameter size S that is less than an inner diameter size I of ferrule 210. While FIGS. 5A-5B illustrate shoulder 312 as a single continuous portion along the inner diameter of ferrule 210, it would be apparent to one skilled in the art that other forms of shoulder 312 may be formed within ferrule 210. For example, shoulder 312 may include one more continuous portions on ferrule 210 and/or discontinuous protrusions such as bumps, ridges, or spikes along an inside surface of ferrule 210.

Figure 6A:
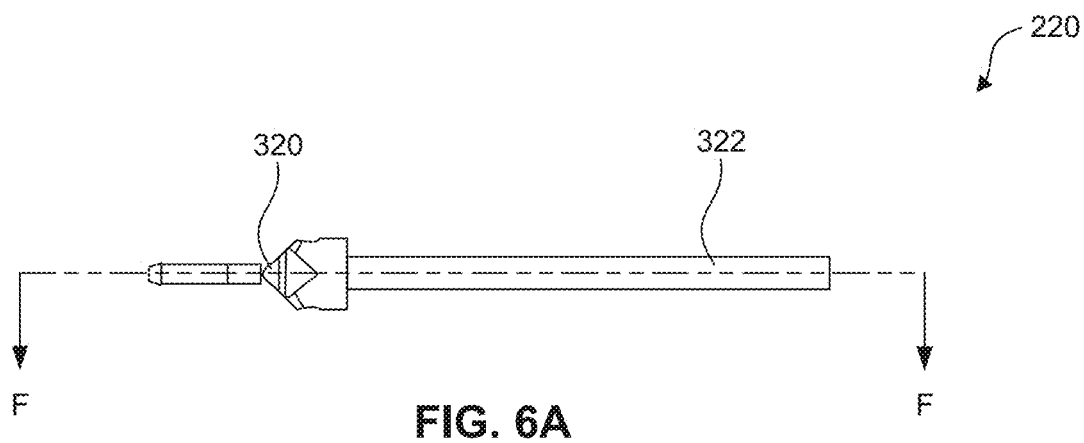
FIG. 6A illustrates an electrode assembly, according to an embodiment of the present disclosure.
Figure 6B:
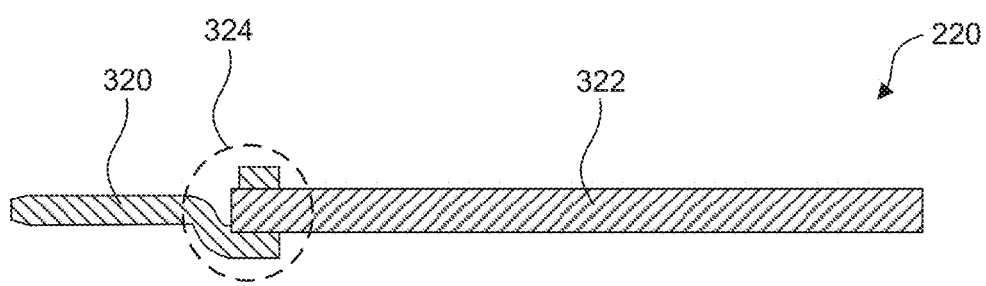
FIG. 6B is a cross-sectional view of the electrode assembly of FIG. 6A taken across section line F-F of FIG. 6A, according to an embodiment of the present disclosure.
Figure 6C:
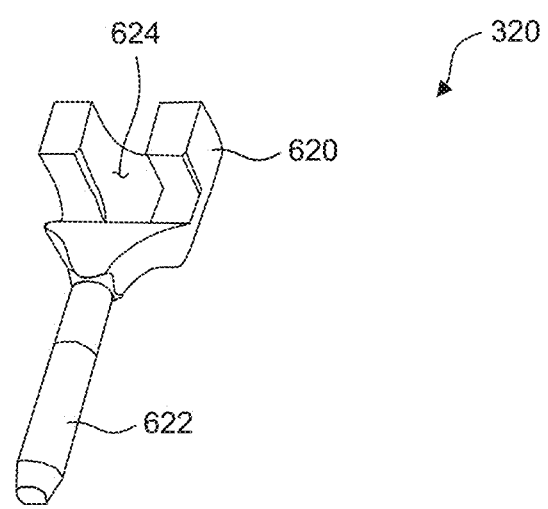
FIG. 6C is a perspective view of a crimp pin, according to an embodiment of the present disclosure.

Electrode assembly 220 is configured to provide an electrical path between an element on an interior of housing 102 (e.g., anode 112) and the external component of the ICD. As shown by FIGS. 3 and 4, electrode assembly 220 extends through ferrule 210. Electrode assembly 220 includes a crimp pin 320 and an electrode wire 322. FIGS. 6A-6C illustrate additional views of electrode assembly 220. FIG. 6B illustrates a cross-sectional view of electrode assembly 220 taken along section line F-F of FIG. 6A. FIG. 6C illustrates a perspective view of crimp pin 320, according to an embodiment of the present disclosure.

Crimp pin 320 is configured to connect to electrode wire 322 within ferrule 210. As shown by FIG. 6C, crimp pin 320 includes a crimp terminal portion 620 and a pin terminal portion 622. Crimp terminal portion 620 includes a contact area 624 configured to receive and crimp to a portion of electrode wire 322. As shown by FIGS. 3-4, crimp terminal portion 620 connects to a distal end of electrode wire 322. Pin terminal portion 622 is configured to provide a contact for electrical connection with an external device, such as an ICD board.

Crimp pin 320 is formed of an electrically conductive material such as nickel, copper, brass, aluminum, or an alloy thereof. Further, a material that forms crimp pin 320 is mechanically formable to facilitate manufacturing of electrode assembly 220. Electrode wire 322 is likewise formed of an electrically conductive material such as aluminum, nickel, copper, brass, or an alloy thereof.

In an embodiment, electrode wire 322 is formed of a first material, and crimp pin 320 is formed of a second material that is different from the first material. For example, electrode wire 322 may be formed of a substantially pure grade of aluminum (e.g., for chemical compatibility with an electrolyte with an aluminum electrolytic capacitor), and crimp pin 320 may be formed of 200 series nickel (e.g., to provide enhanced tensile strength, as compared to high grade aluminum, for mating with external connectors or conductors). In another example, electrode wire 322 may be formed of an aluminum having a first grade, and crimp pin 320 may be formed of an aluminum having a second grade. The second material that forms crimp pin 320 may also be formed of a material that has a high melting point, to prevent melting of crimp pin 320 during manufacturing of electrode assembly 220.

Use of the different materials to form electrode assembly 220 will provide an electrode with greater strength than conventional electrodes. In particular, crimp pin 320 may be formed of a material that is stronger than conventional electrodes, while allowing electrode wire 322 to be formed from a different material that is suitable for use in housing 102. For example, crimp pin 310 may be formed of 200 series nickel having a diameter of 0.019 inches, and electrode wire 322 may be formed of a high purity aluminum having a diameter of 0.025 inches. Accordingly, use of different materials also allows a smaller diameter electrode terminal that is significantly stronger than conventional electrode terminals.

In another embodiment, pin terminal portion 622 may be plated with a third conductive material that is different from the second conductive material that forms crimp pin 320. Examples of the third conductive materials include gold, silver, platinum, or an alloy thereof. The third conductive material of pin terminal portion 622 is configured to improve electrical conduction between electrode assembly 220 and an external device and/or to prevent corrosion of crimp pin 320.

Crimp pin 320 crimps to electrode wire 322 at connection portion 324, as shown by FIGS. 3-4 and 6B. In an embodiment, crimp pin 320 connects to electrode wire 322 by other methods in addition to or aside from crimping. For example, crimp pin 320 may be welded to electrode wire 322 at connection portion 324 instead of, or in addition to, being crimped. In this example, welding crimp pin 320 to electrode wire 322, in addition to being crimped together, further strengthens the connection and electrical conduction between crimp pin 320 and electrode wire 322. In another example, crimp pin 320 may be welded to electrode wire 322 at connection portion 324 without crimping the two portions of electrode assembly 220 together.

Elastomer structure 230 is disposed between ferrule 210 and electrode assembly 220. Elastomer structure 230 is formed of a material that is configured to electrically isolate ferrule 210 from electrode assembly 220 and to prevent leakage of electrolyte 118 between ferrule 210 and electrode assembly 220. As such, elastomer structure 230 encapsulates at least a portion of electrode assembly 220. In particular, elastomer structure 230 encapsulates at least connection portion 324 of electrode assembly 220 to support and strengthen connection point 324. Elastomer structure 230 is further formed of a material configured to withstand heat from a connecting process, such as welding, performed to connect ferrule 210 to housing 102.

Examples of materials used to form elastomer structure 230 include a liquid elastomer such as a silicone or a thermal plastic material including Polyether ether ketone (PEEK). However, it would be apparent to one skilled in the art that other materials may be used for forming elastomer structure 230. Elastomer structure 230 may be formed by an injection molding process to encase electrode assembly 220 within the elastomer 230. However, depending on the specific elastomer used, other methods of molding may be used for encasing electrode assembly 220. For example, conventional injection molding or transfer molding may be used to perform the molding process of the present disclosure.

In an embodiment, elastomer structure 230 includes a recessed area 232 (see FIGS. 2 and 3) configured to receive electrode wire 322 if electrode wire 322 is bent (e.g., at a 90 degree angle) for attachment to a tab 112b, as shown by FIGS. 1C and 4. Recessed area 232 may be formed during a molding process or after the molding process by way of a removal or grinding process.

Figure 7:
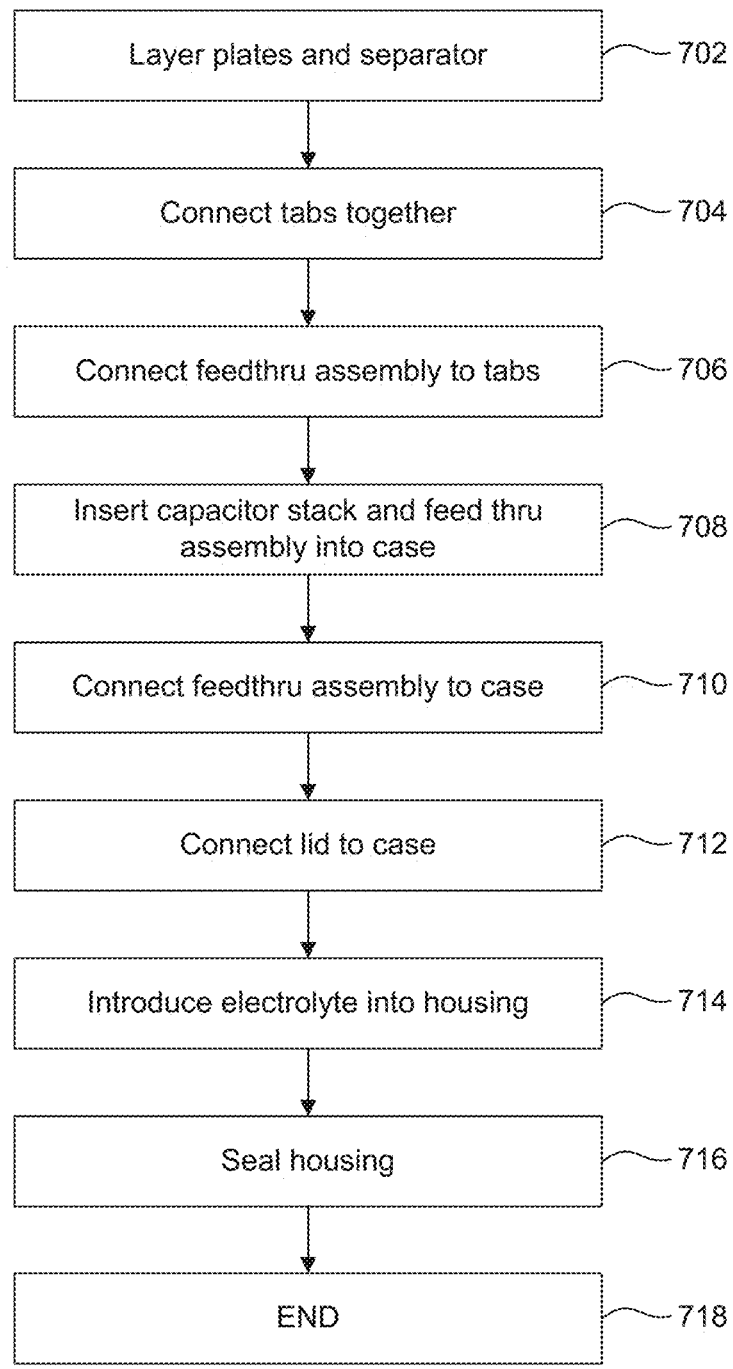
FIG. 7 is a flowchart of a process for manufacturing the electrolytic capacitor of FIGS. 1A-1C, according to an embodiment of the present disclosure.
Figure 8:
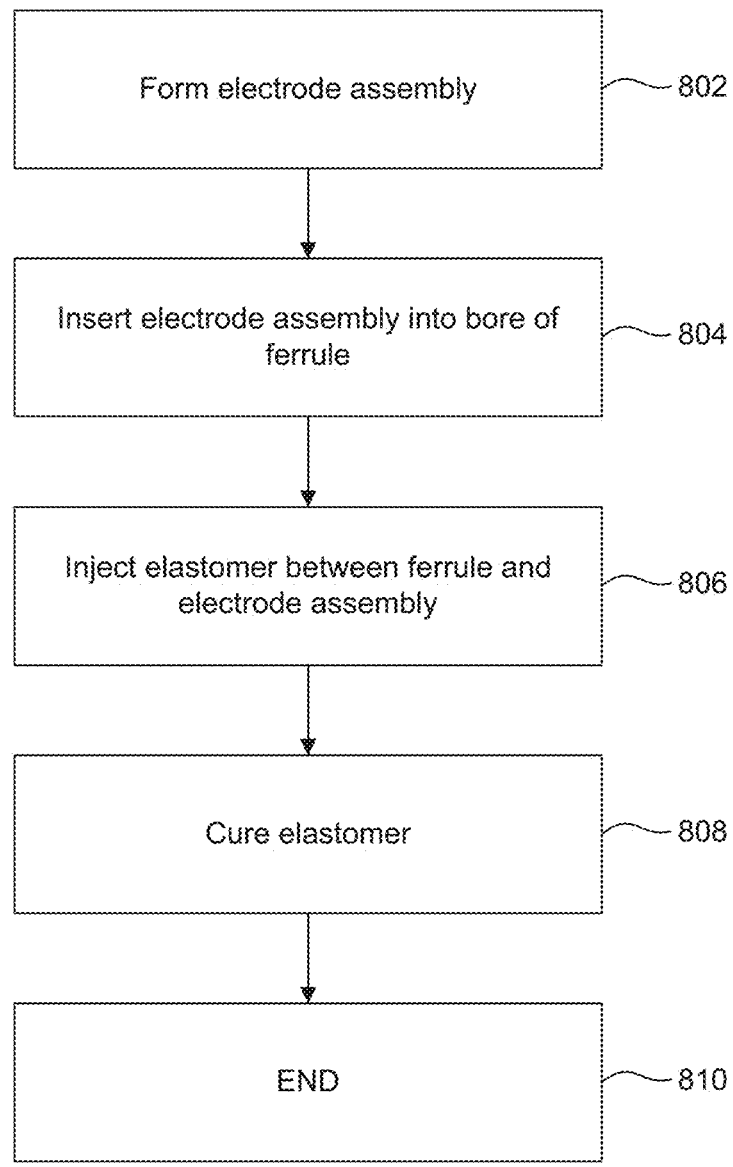
FIG. 8 is a flowchart of a process for manufacturing the feedthru assembly of FIG. 2, according to an embodiment of the present disclosure.

Methods of manufacturing electrical device 100 and feedthru assembly 104 are described with respect to FIGS. 7-8. Although electrical device 100, feedthru assembly 104, and elements have been described, FIGS. 7-8 describe additional details regarding more nuanced features with respect to FIGS. 1-4, 5A-5B, and 6A-6C.

FIG. 7 illustrates a flowchart of a process for manufacturing electrolytic capacitor 100 of FIGS. 1A-1C, according to an embodiment of the present disclosure. Capacitor stack 106 is formed by layering cathode plates 110a, anode plates 112a, and separators 114 (step 702). Capacitor stack 106 is formed such that cathode plates 110a alternate with anode plates 112a and separators 114 are disposed between adjacent cathode plates 110a and anode plates 112a. Next, cathode tabs 110b are connected together to form a single cathode 110, and anode tabs 112b are connected together to form a single anode 112 (step 704). Connection of cathode tabs 110b and anode tabs 112b may be performed by a welding process.

Electrode wire 322 of feedthru assembly 104 is then connected to anode tabs 112b (step 706). During this step, a portion of electrode wire 322 is laser welded to anode tabs 112b. Further, electrode wire 322 may be bent and positioned close to anode tabs 112b such that the bent portion is received within the recessed area 232 of elastomer structure 230. Next, capacitor stack 106 along with feedthru assembly 104 is inserted into housing 102 such that feedthru assembly 104 protrudes through an aperture of the case portion of housing 102 (step 708). During this step, cathode tabs 110b may be connected by, for example, a welding process to housing 102. Feedthru assembly 104 is then connected to the case portion of housing 102 (step 710). Connection of feedthru assembly 104 and housing 102 may be performed by a laser welding process.

A lid portion of housing 102 is attached to the case portion of housing 102 (step 712). The lid portion may be attached by way of a welding process. Next, electrolyte 118 is introduced into housing 102 (step 714). Electrolyte 118 may be introduced through a second aperture (not shown) in housing 102 by way of a vacuum process. The second aperture is then sealed by a plug or an elastomer such as silicone (716). Once sealed, the method of manufacturing electrolytic capacitor 100 ends (step 718).

FIG. 8 illustrates a flowchart of a process for manufacturing feedthru assembly 104 of FIG. 2, according to an embodiment of the present disclosure. Electrode assembly 220 is formed by connecting crimp pin 320 to electrode wire 322 (step 802). Connection of crimp pin 320 and electrode wire 322 may include crimping and/or welding crimp terminal 620 to a portion of electrode wire 322 to form a connected portion 324 of electrode assembly 220. Next, electrode assembly 220 is inserted within a bore of ferrule 210 (step 804). Electrode assembly 220 may be positioned to be substantially concentric with an inside surface ferrule 210. However, in an embodiment, electrode assembly 220 may be positioned off-center, but spaced from an inside surface, of ferrule 210. An elastomer 230 is then injected into a space between electrode assembly 220 and ferrule 210 (step 806). In particular, elastomer 230 encapsulates at least the connected portion of electrode assembly 220 and leaves exposed at least a distal portion of pin terminal portion 622 and a distal portion of electrode wire 322. Injection may be performed by a mold injection method. The elastomer 230 then cures to bond to both the electrode assembly 220 and ferrule 210 (808). Once cured, the method of manufacturing feedthru assembly 104 ends (810).

CONCLUSION

It is to be appreciated that the Detailed Description section, and not the Summary and Abstract sections, is intended to be used to interpret the claims. The Summary and Abstract sections may set forth one or more, but not all, exemplary embodiments of the present apparatuses and methods as contemplated by the inventors, and thus, are not intended to limit the present apparatuses and methods and the appended claims in any way.

Moreover, while various embodiments of the present apparatuses and methods have been described above, it should be understood that they have been presented by way of example, and not limitation. It will be apparent to persons skilled in the relevant art(s) that various changes in form and detail can be made therein without departing from the spirit and scope of the present apparatuses and methods. Thus, the present apparatuses and methods should not be limited by any of the above described exemplary embodiments, but should be defined only in accordance with the following claims and their equivalents.

In addition, it should be understood that the figures, which highlight the functionality and advantages of the present apparatuses and methods, are presented for example purposes only. Moreover, the steps indicated in the exemplary apparatuses and methods described above may in some cases be performed in a different order than the order described, and some steps may be added, modified, or removed, without departing from the spirit and scope of the present system and method.

What is claimed is:

1. A feedthru assembly for an electrolytic device, the feedthru comprising:
  a ferrule having a bore, the bore having a reduced diameter portion forming a shoulder;
  an electrode assembly positioned within the ferrule, the electrode assembly comprising:
    an electrode wire comprising a first portion and a second portion; and
    a pin comprising a first terminal and a second terminal, the first terminal attached to the first portion of the electrode wire to form a connected portion of the electrode assembly, the connected portion being positioned within the bore of the ferrule, the second portion of the electrode wire extending out from the ferrule in a direction away from the pin; and an elastomer disposed in the bore of the ferrule between the ferrule and the electrode assembly, the elastomer configured to electrically isolate the ferrule from the electrode assembly and to encapsulate at least the connected portion of the electrode assembly, the shoulder of the ferrule extending into the elastomer.

2. The feedthru assembly of claim 1, wherein the electrode wire is formed of a first conductive material and the pin is formed of a second conductive material different from the first conductive material.

3. The feedthru assembly of claim 1, wherein the first terminal attaches to the first portion by a crimp method or a welding method.

4. The feedthru assembly of claim 2, wherein the first conductive material comprises aluminum and the second conductive material comprises nickel.

5. The feedthru assembly of claim 4, wherein the pin terminal portion is plated with a third conductive material different from the second conductive material.

6. The feedthru assembly of claim 5, wherein the third conductive material comprises gold.

7. The feedthru assembly of claim 5, wherein the third conductive material is configured to prevent corrosion of the pin.

8. The feedthru assembly of claim 1, wherein the second portion of the electrode wire-includes a bent portion, and the elastomer includes a recessed area in which the bent portion of the electrode wire is positioned.

9. The feedthru assembly of claim 1, wherein the elastomer includes a portion extending out from the ferrule toward the electrode wire, the portion of the elastomer includes a recess, and a bent portion of the electrode wire is positioned in the recess.

10. The feedthru assembly of claim 1, wherein the pin comprises 200 series nickel having a diameter of 0.019 inches, and the electrode wire comprises aluminum having a diameter of 0.025 inches.

11. The feedthru assembly of claim 1, wherein the first terminal attaches to the first portion by a crimp method and a welding method.

12. The feedthru assembly of claim 1, wherein the elastomer comprises a silicone or a thermal plastic material including Polyether ether ketone (PEEK).

* * * * *